US010092445B2

(12) United States Patent
Rathjen et al.

(10) Patent No.: US 10,092,445 B2
(45) Date of Patent: *Oct. 9, 2018

(54) OPHTHALMOLOGIC DEVICE FOR BREAKING DOWN EYE TISSUE

(71) Applicant: SIE AG Surgical Instrument Engineering, Port (CH)

(72) Inventors: Christian Rathjen, Bremen (DE); Wolfgang Zesch, Zurich (CH); Karl Michael Deyerler, Diepoldsau (CH); Holger Lubatschowski, Gehrden (DE); Tammo Ripken, Wunstdorf (DE)

(73) Assignee: SIE AG SURGICAL INSTRUMENT ENGINEERING (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,462

(22) Filed: Jul. 8, 2016

(65) Prior Publication Data

US 2016/0317349 A1  Nov. 3, 2016

Related U.S. Application Data

(63) Continuation of application No. 13/722,145, filed on Dec. 20, 2012, now Pat. No. 9,414,963, which is a
(Continued)

(30) Foreign Application Priority Data

Jun. 9, 2005 (EP) .................................... 05405376

(51) Int. Cl.
*A61B 3/10* (2006.01)
*A61F 9/008* (2006.01)
*A61F 9/009* (2006.01)

(52) U.S. Cl.
CPC .............. *A61F 9/008* (2013.01); *A61F 9/009* (2013.01); *A61F 9/00804* (2013.01);
(Continued)

(58) Field of Classification Search
CPC ......... A61F 9/008; A61B 3/1225; A61B 3/12; A61B 3/1015; A61B 3/103
(Continued)

(56) References Cited

U.S. PATENT DOCUMENTS 3,703,176 A   11/1972   Vassiliadis et al.
4,558,698 A   12/1985   O'Dell
(Continued)

FOREIGN PATENT DOCUMENTS

DE   37 24 282 A1   2/1989
EP   1 486 185 A1   12/2004

*Primary Examiner* — James Greece
(74) *Attorney, Agent, or Firm* — Ostrolenk Faber LLP (57) ABSTRACT

An ophthalmological apparatus includes a base station having a light source generating light pulses, and an application head mountable on an eye having a light projector for focussed projection of the light pulses for punctiform breakdown of eye tissue. The application head has movement drivers moving the light projector in a feed direction and a first scanning direction. A scanner in the base station deflects the light pulses in a second scanning direction. The ophthalmological apparatus includes an optical transmission system transmitting deflected light pulses from the base station to the application head, and superimposing the light pulses deflected in the second scanning direction onto the movement of the light projector in the first scanning direction. Light sources with high light pulse rates, for example femtosecond lasers may be used, without impractical enlargement of the size of the application head.

21 Claims, 6 Drawing Sheets

Related U.S. Application Data continuation of application No. 12/575,336, filed on Oct. 7, 2009, now Pat. No. 8,360,579, which is a continuation of application No. 11/449,626, filed on Jun. 9, 2006, now Pat. No. 7,621,637.

(52) U.S. Cl.
 CPC ............... *A61F 9/00836* (2013.01); *A61F 2009/00872* (2013.01); *A61F 2009/00897* (2013.01)

(58) Field of Classification Search
 USPC ............... 351/205, 206, 246, 221; 606/4–6
 See application file for complete search history.

(56) References Cited

U.S. PATENT DOCUMENTS

| | | | |
|---|---|---|---|
| 5,549,632 A | 8/1996 | Lai | |
| 5,645,550 A * | 7/1997 | Hohla | A61B 18/20 606/1 |
| 5,738,678 A * | 4/1998 | Patel | A61C 1/0046 433/215 |
| 6,626,895 B2 | 9/2003 | Frey et al. | |
| 2002/0049389 A1* | 4/2002 | Abreu | A61B 3/1241 600/558 |
| 2004/0243112 A1 | 12/2004 | Bendett et al. | |
| 2004/0254568 A1* | 12/2004 | Rathjen | A61F 9/00827 606/4 |
| 2005/0177054 A1* | 8/2005 | Yi | A61B 5/055 600/510 |
| 2017/0258320 A1* | 9/2017 | Abreu | A61B 3/1241 |

* cited by examiner

OPHTHALMOLOGIC DEVICE FOR BREAKING DOWN EYE TISSUE

CROSS REFERENCE TO RELATED APPLICATIONS

This is a continuation of U.S. patent application Ser. No. 13/722,145, filed Dec. 20, 2012, which is a continuation of U.S. Pat. No. 8,360,579, issued Jan. 29, 2013, which is a continuation of U.S. Pat. No. 7,621,637, issued Nov. 24, 2009, which claims benefit and priority of European Patent Application No. 05405376.4 filed Jun. 9, 2005, the entire content of each of which is hereby incorporated by reference herein.

TECHNICAL FIELD

The present invention relates to an ophthalmological apparatus for the breakdown of eye tissue. The invention relates, in particular, to an ophthalmological apparatus which comprises a base station having a light source or generating light pulses, and an application head which can be mounted on an eye, which application head is provided with a light projector for the focussed projection of the light pulses for punctiform breakdown of eye tissue, and having movement drivers for moving the light projector in a feed direction and in a first scanning direction.

PRIOR ART

Instances of ametropia such as myopia (short-sightedness), hyperopia (long-sightedness or far-sightedness) or astigmatism can nowadays be permanently corrected by refractive surgical treatment. Refractive surgical treatments are surgical operations on the eye which can change the optical refractive power of the eye with the aim of bringing it as close to a desired value as possible. One of the most important methods in refractive surgery is so-called laser-assisted in situ keratomileusis (LASIK) in which the interior of the cornea is removed with the aid of a computer-controlled eximer laser after a corneal flap has previously been partially severed and folded away. In order to produce the corneal flap, use is made of mechanical microkeratomes in which a driven scalpel cuts the corneal flap. Recently, such corneal flaps can also be cut with the aid of strongly focussed femtosecond laser pulses, which have pulse widths of typically 100 fs to 1000 fs (1 fs=$10^{-15}$ s). The risks existing during use of a mechanically oscillating scalpel are avoided by the use of a femtosecond laser. Such a system is marketed, for example, by IntraLase Corp, in Irvine, Calif., USA under the name of Pulsion FS Laser. The overall size of the known systems having femtosecond lasers is comparable to the overall size of an eximer laser, the disadvantage being that the space required for the eximer laser is required once again in the treatment room for the femtosecond laser system. In addition, after the cutting of the corneal flap by the femtosecond laser system the patient must be transferred to the eximer laser. The overall size of the femtosecond laser is determined, inter alia, by the light source used, the scanner technology and the attendant beam guidance systems.

The laser beam is focussed inside a large stationary lens system by means of beam-deflecting optical elements onto the tissue areas of the eye to be separated. For design reasons, the maximum achievable numerical aperture (NA, proportional to half the sine of the aperture angle of the objective) of the focusing optical system is limited in this case (typically NA=0.2-0.3). For a given work area, for example the entire cornea, the scanning optics (typically f-Theta optics) requires a minimum working distance. In conjunction with the required movement and the achievable size of the beam-deflecting optical elements, the working distance determines a design limit for the diameter of the scanning optics. A further upper design limit for the diameter follows from instances of shadings or collisions with body parts (eyebrows, nose). Even in the case of large diameters, it is always possible to illuminate only a subarea of the optics with a scanning laser beam. The result of this is an upper design limit for the effective useful numerical aperture of the optics. High apertures are desirable because with high NA it is possible to produce small focal points, and thus a smaller cutting zone per pulse. Less gas is produced per pulse in smaller cutting zones than in large cutting zones. More precise cuts can be made by means of smaller gas bubbles since, inter alia, the cutting zones are not substantially deformed by the internal gas pressure. In addition, high NAs require disproportionately less energy per pulse to make a cut. With a lower energy, there is also a reduction in the cavitation bubbles produced by the laser pulse, and this additionally has a positive effect on the cutting quality. Furthermore, the retina is subject to less stress from the more strongly diverging beams downstream of the focal point, given high NAs. A further advantage is that for high NA local contaminants in the vicinity of the corneal surface have less effect in reducing the intensity at the focus.

Patent specification U.S. Pat. No. 5,549,632 describes an ophthalmological apparatus having a laser source for the breakdown of eye tissue, which can be used, inter alia, for cutting corneal flaps. The apparatus in accordance with U.S. Pat. No. 5,549,632 comprises a laser source and a projection head, optically connected to the laser source, in a housing separate from the laser source. Patent specification U.S. Pat. No. 5,549,632 describes an ophthalmological apparatus having a laser source for 20 the breakdown of eye tissue, which can be used, inter alia, for cutting corneal flaps. The apparatus in accordance with U.S. Pat. No. 5,549,632 comprises a laser source and a projection head, optically connected to the laser source, in a housing separate from the laser source. The apparatus in accordance with U.S. Pat. No. 5,549,632 also comprises beam control means which control the beam path of the laser pulses emitted by the laser source such that points in a reference frame fixed relative to the laser source are imaged via an optical connection onto corresponding points in a reference frame fixed relative to the projection head. The optical connection is designed as an articulated mirror arm so that the light pulses deflected by the beam control means can be imaged relative to the reference frame of the hand-held appliance. The connection of the projection head to an applanation plate which can be permanently connected to the eye means that the fixed reference frame of the projection head in accordance with U.S. Pat. No. 5,549,632 is permanently imaged onto the applanation plate and thus onto the eye. In accordance with U.S. Pat. No. 5,549,632, the laser pulses are led to desired positions of the eye by using the beam control means to control the position of the pulsed laser beam relative to the applanation plate, and to image it onto the eye via the optical connection and the optical projection system of the projection head. For example, in order to carry out cuts of 5 to 15 mm in length, the optical projection system of the projection head must have optical lenses whose diameter is greater than the diameter of the eyeball. A projection head of such large dimension will cover the view onto the eye to be treated. Furthermore, the numerical aperture of the apparatus in accordance with U.S. Pat. No. 5,549,632 is small, as may be seen from the relatively small convergence of the beams. Large lens systems also have the disadvantage of causing apparatuses to become heavy and unwieldy, thus complicating manual holding and application.

Patent application EP 1 486 185 describes an ophthalmological apparatus for the breakdown of eye tissue, which comprises an application head which can be mounted on the eye and is provided with a light projector. The light projector is moved with the aid of movement driver in order to bring the focal point to the desired site for tissue breakdown. According to EP 1 486 185, a fine movement of the focal point can additionally be superimposed on the translatory movements of the light projector by means of optical microscans. In order, however, to be able to deflect grossly expanded, nonconvergent light beams advantageous for cutting, there is a need for relatively large mirrors (for example 14 mm) which must be tilted by relatively large angles (for example 4 degrees). Such large scanner systems do not, however, permit high speeds given the present prior art, and cannot be of compact design. If the aim is to avoid the above-named disadvantages of a large overall size of the application head, and if the aim is to prevent the same site in the eye tissue from being hit repeatedly by the light pulses, it is, however, possible to make use in the application head of simply optical microscans for low pulse rates. However, low pulse rates signify an operation procedure which is slowed down and thus less stable.

SUMMARY OF THE INVENTION

It is an object of the present invention to propose a novel ophthalmological apparatus for the breakdown of eye tissue, which does not have at least certain disadvantages of the prior art.

In accordance with the present invention, these objects are achieved, in particular, by the elements of the independent claims. Further advantageous embodiments also follow from the dependent claims and the description.

The ophthalmological apparatus comprises a base station having a light source for generating light pulses, and an application head which can be mounted on an eye. The application head is provided with a light projector for the focussed projection of the light pulses for punctiform breakdown of eye tissue, and having movement drivers for moving the light projector in a feed direction and in a first scanning direction. The application head comprises, for example, a contact body which can be mounted on the eye, is transparent at least in parts and is configured and arranged so that it sets a region of the eye whose contact is made in the mounted state in a fashion equidistant from a working surface. The application head also has, for example, fastening means for fixing the application head at the eye by low pressure.

The above-named objects are achieved by the present invention by virtue of the fact that, in particular, the ophthalmological apparatus comprises beam deflecting means, arranged in the base station, for deflecting the light pulses in a second scanning direction, for example, a rotatably supported mirror having drive means, and has an optical transmission system for transmitting deflected light pulses from the base station to the application head, and for superimposing the light pulses deflected in the second scanning direction onto the movement of the light projector in the first scanning direction. The rotatably supported mirror is configured, for example, as a polygonal mirror with a number of facets. In an alternative variant, the beam deflecting means comprise AOM (acoustic/optical modulators) elements. The movement of the light projector (slow scanning) in the first scanning direction is preferably slower by a multiple by comparison with a movement of the light pulses (fast scanning) which is caused by the deflection of the light pulses in the second scanning direction. The exporting of the scanner comprising the rotatably supported mirror and the drive means into the base station, and the optical transmission and superimposition of the light pulses, deflected in the second scanning direction by means of the scanner, onto the slow scanning movement of the light projector in the application head enables a substantially smaller overall size of the application head than a configuration of the allocation head with a scanner for fast scanning movements. It is possible to use light sources with high light pulse rates, for example femtosecond lasers, without the need for impractical enlargement of the overall size of the application head owing to a scanner for fast scanning movements. The overall size of the application head can be dimensioned such that the application head can be applied in the treatment room to a patient who is positioned under an eximer laser system, that is to say the application head can be inserted between the eximer laser system and patient such that there is no need during the entire treatment for either the patient or the eximer laser system to be displaced and positioned anew. By means of the exported scanner for fast scanning movements, it is possible to prevent the same site in the eye tissue from being repeatedly hit by the light pulses when use is made of light sources with high light pulse rates. By using light sources with high light pulse rates, it is possible to carry out the operational procedure more quickly and thus in a more stable fashion than when use is made of light sources with low light pulse rates, something which increases the accuracy of treatment and reduces the burden on the eye.

In a preferred variant design, fitted on the base station is an articulated arm which can be fastened to the application head with an end diverted from the base station, and the optical transmission system is arranged in the interior of the articulated arm. The articulated arm enables flexible positioning of the application head in conjunction with transferral of the weight of the application head to the base station and, as a result thereof, relief for the eye which is to be treated.

The articulated arm preferably comprises a number of arm elements, in each case two of the arm elements being connected by means of an articulated module such that they can be rotated in parallel planes relative to one another, at least one of the arm elements being rotatable about its longitudinal axis, and deflecting mirrors being fitted in the articulated modules in order to transmit the deflected light pulses from one arm element to the other arm element.

In one variant design, means for weight compensation are fitted on at least one moveable arm element of the articulated arm in order to keep the application head in equilibrium, for example counterweights, springs or actuators.

In a preferred variant design, the optical transmission system comprises a rotation element, which is configured, for example, as a K-mirror, for rotating a scanning plane defined by the deflected light pulses about an optical transmission axis. The rotation element is preferably arranged in the base station. The rotation element enables image rotations which are caused by the articulated mirror arm to be compensated reliably in a simple way.

In one variant design, the application head comprises a transmitter for emitting a light mark for determining a desired alignment of the second scanning direction. The light mark is arranged such that it can be transmitted to the base station via the optical transmission system. In addition, the base station comprises a light sensor module and a regulation module which is connected to the light sensor module. The regulation module is set up to control the rotation element so that the scanning plane defined by the deflected light pulses is rotated about the optical transmission axis until the desired alignment of the second scanning direction has been reached.

In one variant design, the light sensor module comprises two light sensors for detecting the light mark transmitted via the optical transmission system to the base station and the regulation module is set up to control the rotation element on the basis of a sum and/or a difference of luminosities, determined by the light sensors, of the detected light mark.

In one alternative variant design, at least certain ones of the arm elements are provided with a rotation sensor which are connected to a regulation module for the purpose of feeding back a degree of rotation to the relevant arm element. In this alternative variant design, the regulation module is set up to control the rotation element so that the scanning plane defined by the deflected light pulses is rotated about the optical transmission axis until a desired alignment of the second scanning direction has been reached.

In a preferred variant design, the base station comprises a control module which is set up to control the movement drivers so that the light projector traverses a working surface (cutting surface) equidistantly in lines, which run in the first scanning direction, with a defined line feed in the feed direction. In this case, the optical transmission system and the light projector are optically coupled such that the light pulses deflected in the second scanning direction are superimposed on the lines such that the punctiform breakdown of eye tissue in the working surface is performed coherently.

In one variant design, the light source and the light projector are set up for the punctiform breakdown of eye tissue at a focal point in the interior of the eye. In particular, the light source comprises a femtosecond laser. A femtosecond laser comprises a laser generator for generating laser pulses with pulse widths from 1 fs to 1 ps (1 fs=$\frac{1}{1000}$ ps=$10^{-15}$ s). Laser pulses with such pulse widths enable the targeted punctiform breakdown of tissue in the interior of the eye tissue, mechanical and thermal side effects in the surrounding tissue such as are known from longer pulse widths being greatly reduced. In addition, the base station comprises a control module which is set up to control the movement drivers so that the light pulses which are deflected in the second scanning direction and are superimposed on the movement of the light projector in the first scanning direction separate from the remaining eye tissue a tissue flap which remains connected to the eye in a residual area.

BRIEF DESCRIPTION OF THE DRAWINGS

A design of the present invention is described below with the aid of an example. The example of the design is illustrated by the following attached figures.

Ways Of Implementing The Invention

Mutually corresponding components are denoted in FIGS. 1 to 8 by identical reference symbols.

Figure 1:
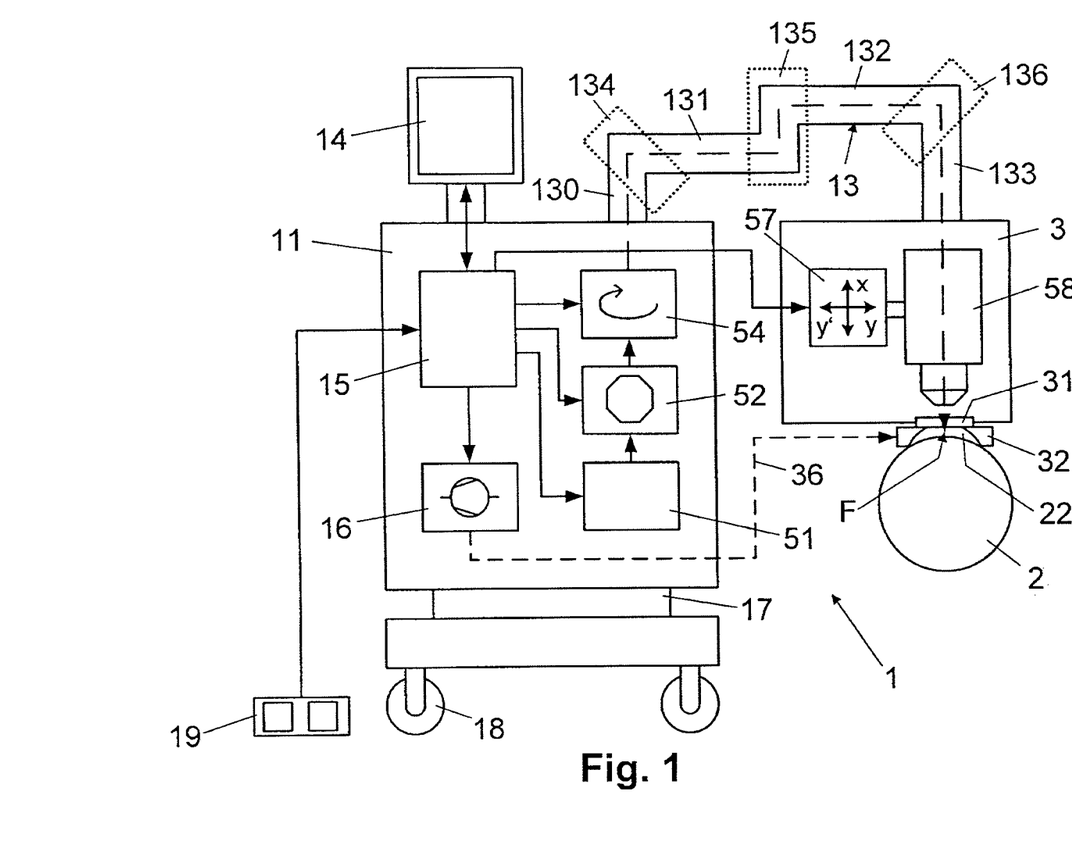
FIG. 1 shows a block diagram which schematically illustrates an ophthalmological apparatus which has an application head which is connected to a base station via an articulated arm.

In FIG. 1, the reference numeral 1 denotes an ophthalmological apparatus which comprises a base station 11 and an application head 3 which are interconnected via an articulated arm 13.

The base station 11 is of mobile configuration and has a lockable running gear 18. In addition, the base station 11 has a height adjusting means 17 which enables the height of the base station 11 to be adjusted. The base station 11 also comprises an electronic control module 15 which is set up to receive control signals from a user via a foot switch 19 arranged externally in relation to the housing of the base station 11. The control module 15 can also be operated and controlled by a user via a display and operating unit 14. The base station 11 further has a vacuum pump 16, a light source 51, a scanner 52 and a rotation element 54 which are controlled by the control module 15. The control module 15 also controls the movement drivers 57 of the application head 3.

The vacuum pump 16 is connected to a suction unit 32 of the application head 3 via a vacuum connecting line 36. The application head 3 can be fixed at the eye 2 to be treated via the suction unit 32, which is, for example, configured in the form of a suction ring. During fixing of the application head 3 at the eye 2, the surface of the area of the eye 2 to be treated is applanated by a contact body 31 of the application head 3 or, depending on the shaping of the contact body 31, is given the form of a suction ring. During fixing of the application head 3 at the eye 2, the surface of the area of the eye 2 to be treated is applanated by a contact body 31 of the application head 3 or, depending on the shaping of the ontact body 31, is given another desired shape, for example concave or convex. The contact body 31 therefore serves as a reference body which brings the eye tissue 22 to be processed into a defined position relative to the application head 3.

Figure 4:
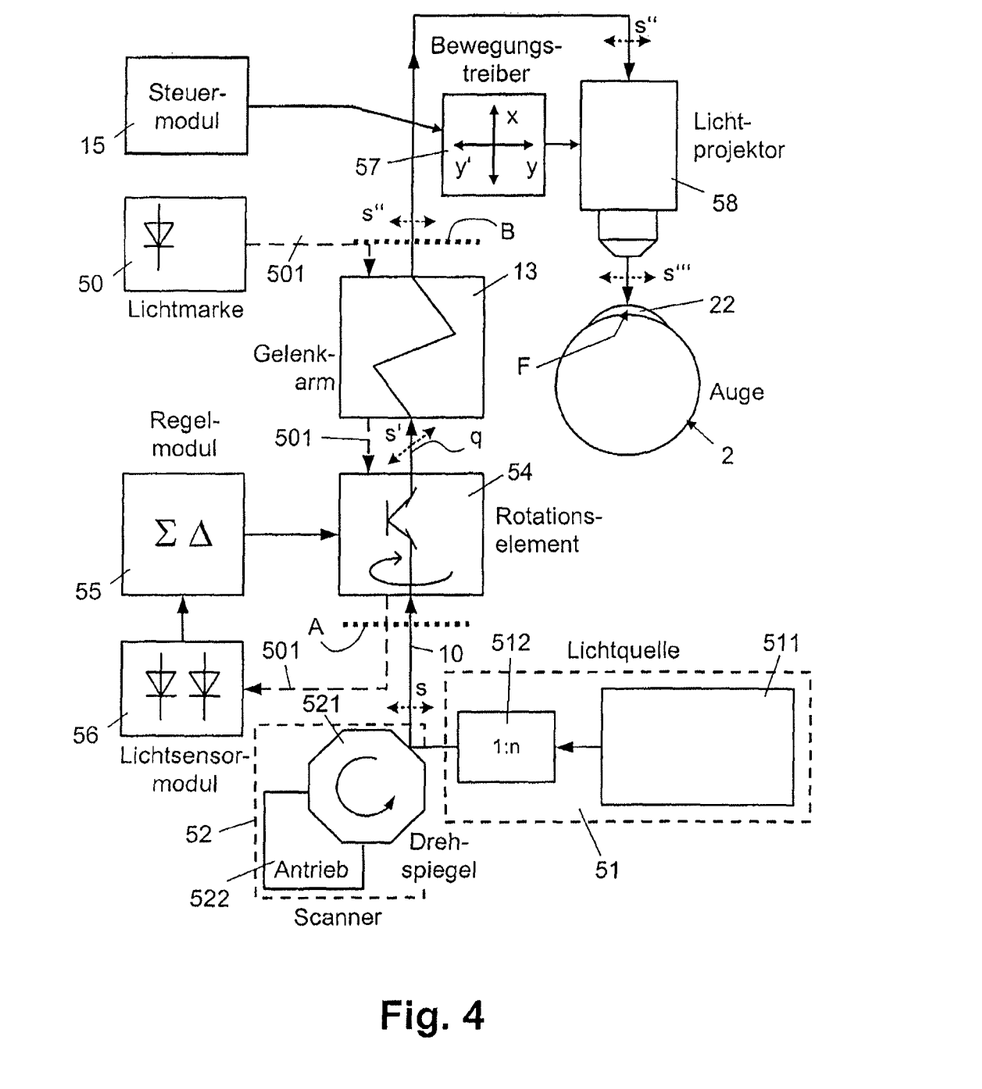
FIG. 4 shows a block diagram which illustrates diagrammatically the cooperating functional elements of the ophthalmological apparatus.

As illustrated diagrammatically in FIG. 4, the light source 51 has a femtosecond laser 511, that is to say a laser generator for generating laser pulses with pulse widths in the femtosecond range from 1 fs to 1 ps (1 fs=$\frac{1}{1000}$ ps=$10^{-15}$ s). The light source 51 also comprises a beam expander 512 which is connected to the femtosecond laser 511 and serves a purpose of expanding the beam diameter for transmission via the downstream optical transmission system, and thus of reducing the divergence. Moreover, expansions/reductions of the beam downstream of the mirror permit an adaptation of the scanning angle.

The movement drivers 57 preferably comprise a drive element for a feed direction x and a drive element for a scanning direction y, y', for example piezomotors. The application head 3 also comprises a light projector 58 which is optically connected to the light source 51, as is set forth in more detail below, and which is set up as a cutting objective for the focussed projection of light pulses for the punctiform breakdown of tissue at a focus point F in the interior of the eye tissue 22. As is to be seen from FIG. 3, the movement 30 drivers 57 are set up and arranged to move the light projector 58 mechanically in a fashion equidistant from (preferably parallel to) a cutting surface 21 (work surface) so that the focal point F is displaced in the cutting surface 21. In one variant design, the movement drivers 57 further comprise a drive element in order, for the purpose of setting the depth of the focal point F, to move the light projector 58 perpendicular to a plane defined by the feed direction x and scanning direction y, y'.

The application head 3 is removably connected to the articulated arm 13 via a connecting piece 133, for example by means of a screwed connection or a snap lock. Via a connecting piece 130, the articulated arm 13 is fitted on the base station 11 at the end of the articulated arm 13 averted from the application head 3. The articulated arm 13 has an articulated module, denoted as shoulder articulation 134, which moveably connects an arm element denoted as upper arm 131 to the connecting piece 130. The articulated arm 13 has an articulated module, denoted as hand articulation 136, which moveably connects an arm element denoted as forearm 131 to the connecting piece 133. The articulated arm 13 also has an articulated module, denoted as elbow articulation 135, which moveably connects the upper arm 131 to the forearm 132.

Figure 2:
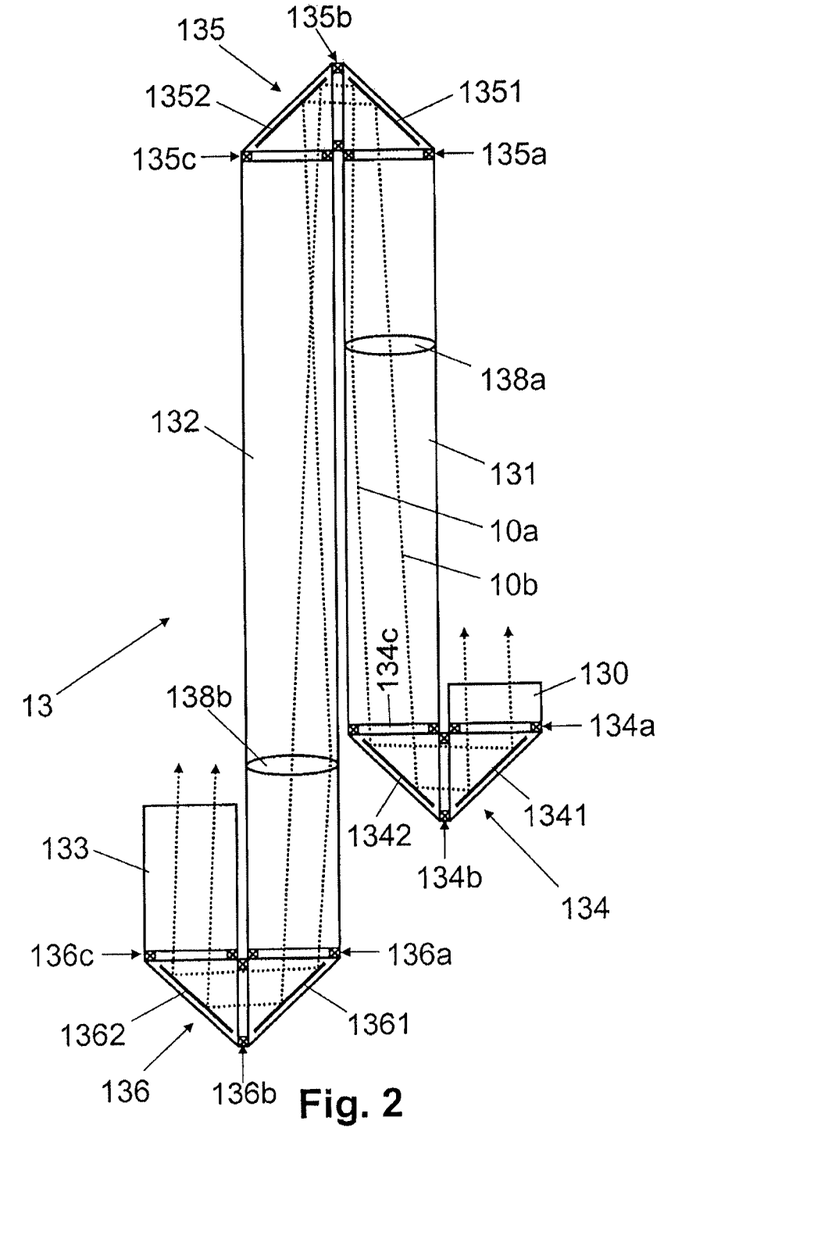
FIG. 2 shows a diagrammatic cross section of the articulated arm with an optical transmission system fitted therein.

As is illustrated diagrammatically in FIG. 2, the shoulder articulation 134, the elbow articulation 135 and the hand articulation 136 respectively comprise a rotary joint 134b, 135b and 136b which enables the arm elements fitted on the relevant articulated module to rotate relative to one another in parallel planes. Moreover, the shoulder articulation 134, the elbow articulation 135 and the hand articulation 136 respectively comprise further rotary joints 134a and 134c, 135a and 135c, and 136a and 136c, which enable the arm elements fitted on the relevant articulation module to rotate about their longitudinal axes, it also being possible to eliminate one of the articulations 134c/135a or 135c/136a. The articulated arm also comprises an optical transmission system which comprises lens systems 138a, 138b and deflecting mirrors 1341, 1342, 1351, 1352, 1361, 1362. The deflecting mirrors 1341, 1342, 1351, 1352, 1361, 1362 are arranged in pairs in one of the articulation modules, each of the deflecting mirrors 1341, 1342, 1351, 1352, 1361, 1362 being arranged at an angle of 45° to the longitudinal axis of the arm element directly connected to the relevant articulated module, and in each case the pair of deflecting mirrors 1341, 1342, 1351, 1352, 1361, 1362 arranged in one of the articulated modules being arranged in a mutually perpendicular fashion in the collapsed position illustrated in FIG. 2. As is illustrated diagrammatically by means of the exemplary beams 10a, 10b, the lens systems 138a, 138b and the reflecting 10 mirrors 1341, 1342, 1351, 1352, 1361, 1362 enable a bidirectional beam path from one end of the articulated arm 13 to the other end of the articulated arm 13 so that light beams can be transmitted in all possible alignments of the articulated arm 13 both from the base station 11 to the application head 3 and from the application head 3 to the base station 11. The bidirectionality of the optical transmission system of the articulated arm 13 is important, in particular, in the context of the transmission of a reference light mark from the application head 3 to the base station 11, something which is described in more detail later.

Figure 3:
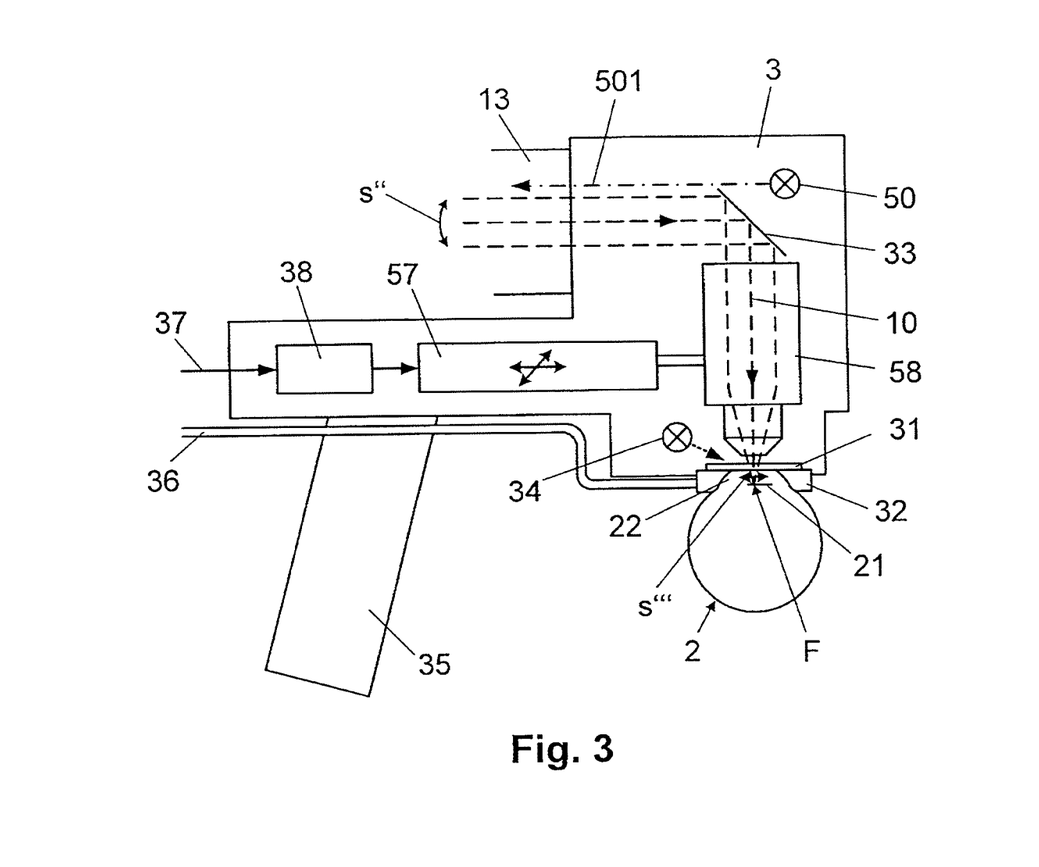
FIG. 3 shows a diagrammatic cross section of the application head which is fitted at an eye by means of a suction unit.

As is illustrated in FIG. 3, the application head 3 has a handle 35 for manually positioning the application head 3. The application head 3 also comprises an electronics module 38 which is connected to the control module 15 of the base station 11 via a connecting interface 37, and drives the movement drivers 57. The application head 3 also has an eye illuminating means 34 for projecting onto the eye 2 reference marks which serve as positioning aids. The application head 3 is provided with a viewing window in order to visualize the reference mark for the user when the application head 3 is mounted on the eye 2. The application head 3 also comprises a transmitter 50 for emitting a light mark, for example an LED (light-emitting diode). The transmitter 50 produces the light mark in the form of a reference light beam 501 which is transmitted to the base station 11 from the application head 3 via the optical transmission system of the articulated arm 13. As is to be seen from FIG. 3, the application head 3 comprises a deflecting mirror 33 which head 3 via the optical transmission system of the articulated arm 13. As is to be seen from FIG. 3, the application head 3 comprises a deflecting mirror 33 which is arranged such that a laser beam 10 which is received from the base station 11 via the optical transmission system of the articulated arm 13 is deflected to the light projector 58 so that a fast scanning movement of the laser beam 10 in the scanning direction s" is superimposed on the mechanical movement of the light projector 58, which is produced by the movement drivers 57. The consequence of this is to produce a combined scanning movement s''' of the focal point F which is based on the quick scanning movement in the scan direction s" of the laser beam 10 and a slow mechanical movement of the light projector 58 in the feed direction x and in the scanning direction y, y', and produces the cutting surface 21 in the eye tissue 22.

Figure 6:
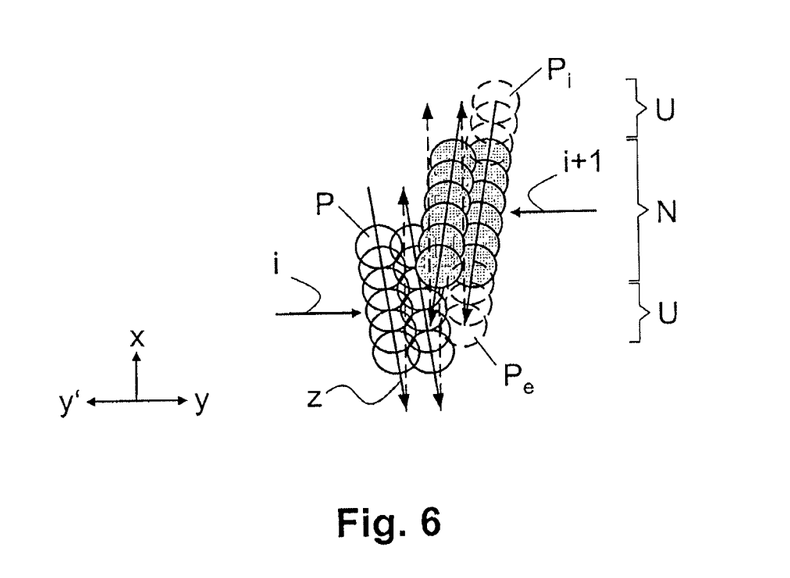
FIG. 6 illustrates the superimposition of a fast scanning movement of a pulsed laser beam onto a slower mechanical movement of the laser beam.

As is illustrated diagrammatically in FIG. 4, the fast scanning movements of the laser beam 10 are produced by the scanner 52. The scanner 52 has a rotatably supported mirror 521 and drive means 522 which rotate the rotatable mirror 521 about a rotation axis. The light pulses emitted by the light source 51 are deflected in the scanning direction s by the rotating mirror 521. The mirror 521 is preferably a polygonal mirror with a number of facets, for example an octagonal pyramidal mirror. As illustrated in FIG. 6, the light pulses are deflected anew by each facet, starting from an initial position $P_i$ to as far as an end position $P_e$. After the light beam formed by the light pulses strikes the end of the facet of the rotating mirror 521, the light beam is deflected again by the next facet from the initial position $P_i$ as far as the end position $P_e$. The laser beam 10, which is formed by the light pulses deflected in the scanning direction s, is transmitted via the rotation element 54, the silvered articulated arm 13 and the deflecting mirror 33 onto the light projector 58 of the application head 3, as is described in more detail below. As illustrated in FIG. 6, the superimposition of the deflected light pulses onto the mechanical movement of the light projector 58 results in a projection of light pulses which follows a saw-tooth curve in the scanning direction y or y' of the curve mechanical movement of the light projector 58. In one variant design, the base station 11 comprises a further scanner in order to deflect the light pulses emitted by the light source 51 by means of a further rotating mirror perpendicular to the scanning direction s.

The laser beam 10 with the light pulses deflected by the scanner 52 strikes the rotation element 54, for example a K-mirror, which can be rotated by a rotation driver about an optical axis. The rotation element 54 enables the scanning plane, in which the light pulses deflected in the scanning direction s run, to rotate about the optical axis q so that it is possible to compensate a rotation of the scanning direction caused by the optical transmission system of the articulated arm 13. The rotation element 54 therefore rotates the original orientation of the scanning direction s into a compensated scanning direction s' which is rotated by the optical transmission system of the articulated arm 13 into the resulting scanning direction s'', which corresponds to the original orientation of the scanning direction s. The extent of the rotation by the rotation element 54 that is required to compensate the scanning direction is determined on the basis of the reference light beam 501 which is transmitted to the base station 11 by the transmitter 50 from the transmitter plane B via the optical transmission system of the articulated arm 13. The base station 11 comprises a light sensor module 56 for receiving the reference light beam 501 in the receiver plane A. The regulation module 55 controls the rotation element 54 on the basis of the received reference light beam 501, as is described below with reference to FIGS. 7 and 8.

Figure 7:
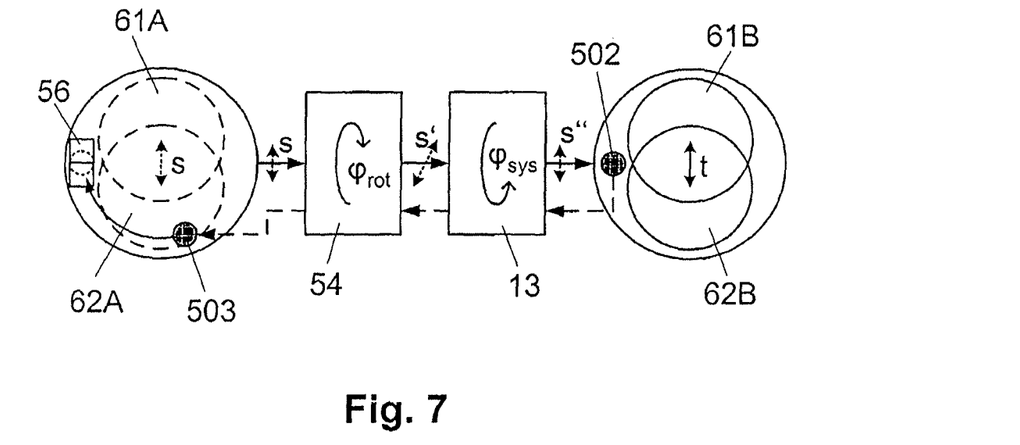
FIG. 7 shows a block diagram which illustrates schematically the transmission of a light mark as positioning aid to a receiver plane from a transmitter plane via the optical transmission system of the articulated arm and via a rotation element.

In FIG. 7, the reference symbol B denotes the transmitter plane in which the light mark 502 produced by the transmitter 50, and cross sections 61B, 62B of light pulses are visible. The desired alignment of the fast scanning movement is denoted by t. The reference symbol A denotes the receiver plane in which the received light mark 503 produced via the transmitter 50, and cross sections 61A, 62A of light pulses in the desired alignment are visible. In addition, the light sensor module 56, which has two light sensor elements, is arranged in the receiver plane A. As is to be seen from FIG. 7, the original scanning direction s is rotated by the rotation element 54 by the rotation angle $\varphi_{rot}$. The scanning direction s' rotated by the rotation element 54 is rotated by the optical transmission system of the articulated arm 13 by the angle $\varphi_{sys}$ so that, given optimum regulation of the rotation element 54, the sum of the rotation angle $\varphi_{rot}$ and the angle $\varphi_{sys}$ vanishes, and the scanning direction s'' emanating from the articulated arm 13 therefore corresponds to the original scanning direction s.

Figure 8:
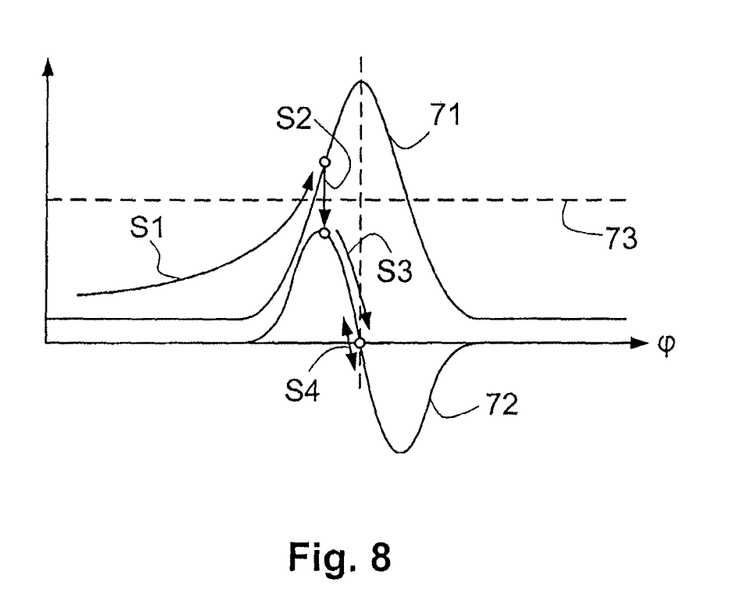
FIG. 8 shows the profile of an aggregate signal and of a difference signal which are formed in the receiver plane on the basis of the received light mark.

As illustrated in FIG. 8, the regulation module 55 uses the signal values measured by the two light sensor elements of the light sensor module 56 to form an aggregate signal 71 and a difference signal 72. In a first step S1, the regulation module 55 carries out a search by increasing the rotation angle $\varphi_{rot}$ until the received light mark 503 is rotated in the region of the light sensor module 56 so that the aggregate signal 71 exceeds a defined threshold value 73. Thereafter, in step S2 the regulation module 55 switches over into a regulation mode and regulates the rotation angle $\varphi_{rot}$ in step S3 until the difference signal 72 vanishes. If the difference signal 72 vanishes in the regulation mode, the position of the received light mark 503 agrees with the position of the light sensor module 56, and consequently the scanning directions'', emanating from the articulated arm 13, of the fast scanning movement corresponds to the desired alignment t. In step S4, a continuous fine regulation is performed to compensate rotations of the scanning direction which are caused by movements of the articulated arm 13.

In an alternative variant design, instead of the transmitter 50 and the light sensor module 56, the ophthalmological apparatus 1 comprises rotation sensors which are respectively fitted in the rotatable arm elements of the articulated arm 13. In order to feed back the degree of rotation and the direction of rotation of the relevant arm element about its longitudinal axis, the rotation sensors are connected to the regulation module 55. In this variant design, the regulation module 55 determines the rotation angle $\varphi_{rot}$ for the rotation element 54 on the basis of the feedback from the individual arm elements.

Figure 5:
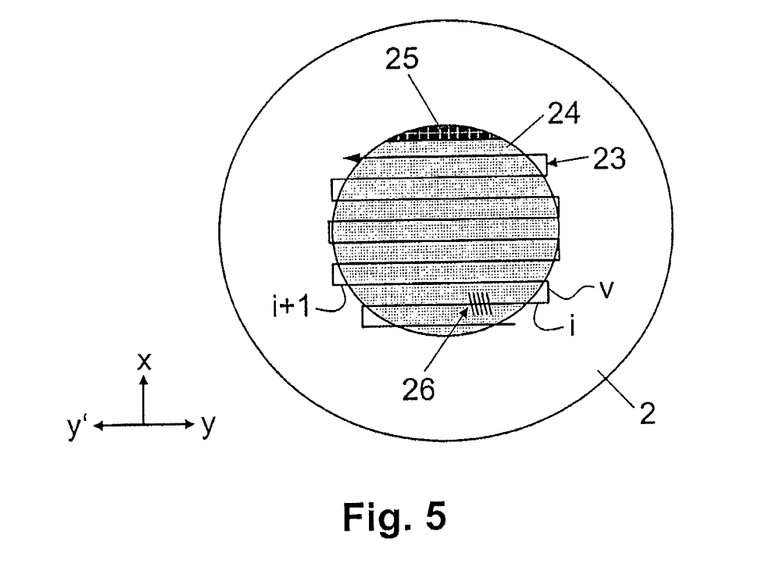
FIG. 5 shows a view of an eye from which there has been separated by means of a fast scanning movement, superimposed on a mechanical movement, of a laser beam a tissue flap which remains connected to the eye in a residual area.

The control module 15 and the electronics module 38 are preferably implemented as programmed software modules for controlling one or more processors of the base station 11. The person skilled in the art will understand that the control module 15 and the electronics module 38 can also be designed partially or completely as hardware. The control module 15 and the electronics module 38 are set up to control the movement drivers 57 so that, as illustrated in FIG. 5, the light projector 58 is moved along a meandering scanning pattern 23. The scanning pattern 23 of the light projector 58 is formed by translations along scanning lines i, i+1 in the scanning direction y and y' respectively, and by translations for the line feed v (line spacing) in the feed direction x. The cutting surface 21 is processed by the focus F of the projected light beam in a fashion covering the surface (without gaps) by the superimposition of the scanning pattern 26 of the fast scanning movement of the laser beam 10 formed by the light pulses onto the meandering scanning pattern 23 of the mechanical movement of the light projector 58. For example, it is possible in the applanated area 24 of the eye 2 for a tissue flap to be separated from the remaining eye tissue 22, which flap remains connected to the eye 2 in a residual area 25 (a so-called hinge). The cutting of such a flap is the preferred application, but the apparatus 1 proposed can also be used for other surgical operations.

As illustrated in FIG. 6, the deflecting speed of the scanner 52 is preferably determined such that consecutive light pulses P partially overlap. The speed of the mechanical translation in the scanning direction y, y' and in the feed direction x (slow scanning movement) is slower by a multiple than the speed of the movement, caused by the deflection of the light pulses in the scanning direction s, of the light pulses (fast scanning movement). The speed of the mechanical translation in the scanning direction y, y' is preferably determined so that the light pulses P of consecutive lines z of the fast scanning movement partially overlap. The line feed v of the mechanical scanning pattern 23 is preferably determined so that the scanning pattern 26 of the fast scanning movement of a scanning line i partially overlaps with the scanning pattern 26 of the fast scanning movement of the subsequent scanning line i+1. Laser sources with pulse repetition frequencies in the range between 100 kHz and 100 MHz are used to produce precise cuts in conjunction with short cutting times. The diameter of a light pulse is 1-5 μm, for example, and the rotation or deflection speed of the scanner 52 is 100-1000 Hz, for example, something which corresponds to a deflection speed of the light pulses of the order of magnitude of 1-10 m/s, the speed of the mechanical translation in the scanning direction y, y' is 1-10 mm/s, for example, and the line feed v of the mechanical scanning pattern is 0.5-1 mm, for example. The scanning range N used, which is indicated in FIG. 6, is determined, for example, by stops or mechanical or electronic shutters which are arranged so that the unused scanning regions U are masked out, for example, upstream of the rotation element 54.

In conclusion, it may be stated that the person skilled in the art will understand that the proposed apparatus 1 is not limited to the orthogonal scanning raster as described, but that the apparatus 1 also renders possible other scanning rasters, for example spiral or circular scanning patterns.

Finally, it may be remarked that the proposed apparatus 1 is integrated in an eximer laser system in one variant design, for example, the base station 11 is integrated in the couch of the eximer laser system.

What is claimed:

1. An ophthalmological apparatus, comprising:
a light source configured to generate light pulses;
a scanner configured to deflect the light pulses in a scanning direction;
an articulated arm;
a light projector connected to the articulated arm and configured for focused projection of the light pulses;
an optical transmission system arranged in the articulated arm and configured to transmit deflected light pulses to the light projector;
a transmitter configured to emit a reference light beam for determining a desired alignment of the scanning direction; and
a light sensor module configured to receive the reference light beam from the transmitter;
wherein the transmitter is arranged to transmit the reference light beam to the light sensor module via the optical transmission system in the articulated arm.

2. The ophthalmological apparatus of claim 1, wherein the ophthalmological apparatus further comprises a regulation module connected to the light sensor module and configured to use the reference light beam received by the light sensor module to regulate for the desired alignment of the scanning direction.

3. The ophthalmological apparatus of claim 1, wherein the ophthalmological apparatus further comprises a regulation module connected to the light sensor module and configured to use the reference light beam received by the light sensor module to compensate for deviations from the desired alignment of the scanning direction caused by movements of the articulated arm.

4. The ophthalmological apparatus of claim 1, wherein the ophthalmological apparatus further comprises a regulation module connected to the light sensor module and configured to use the reference light beam received by the light sensor module to control rotation of a scanning plane, defined by the deflected light pulses, about an optical transmission axis until the desired alignment of the scanning direction has been reached.

5. The ophthalmological apparatus of claim 1, wherein the ophthalmological apparatus further comprises a rotation element configured to rotate a scanning plane defined by the deflected light pulses about an optical transmission axis; and the ophthalmological apparatus further comprises a regulation module connected to the light sensor module and configured to control the rotation element such that the scanning plane defined by the deflected light pulses is rotated about the optical transmission axis until the desired alignment of the scanning direction has been reached.

6. The ophthalmological apparatus of claim 5, wherein the regulation module is configured to control rotation of the scanning plane to compensate rotations of the scanning direction which are caused by movements of the articulated arm.

7. The ophthalmological apparatus of claim 5, wherein the rotation element is configured as a K-mirror.

8. The ophthalmological apparatus of claim 5, wherein the ophthalmological apparatus further comprises a base station, and the rotation element is arranged in the base station.

9. The ophthalmological apparatus of claim 1, wherein the transmitter is arranged downstream of the optical transmission system of the articulated arm, and the light sensor module is arranged upstream of the optical transmission system of the articulated arm.

10. The ophthalmological apparatus of claim 1, wherein the light sensor module comprises two light sensor elements configured to detect the reference light beam from the transmitter.

11. The ophthalmological apparatus of claim 10, wherein the light sensor elements are configured to determine luminosities from the reference light beam; and the ophthalmological apparatus further comprises a regulation module connected to the light sensor module and configured to regulate for the desired alignment of the scanning direction based on a sum and/or a difference of the luminosities.

12. The ophthalmological apparatus of claim 1, wherein the transmitter comprises an LED for emitting the reference light beam.

13. The ophthalmological apparatus of claim 1, wherein the ophthalmological apparatus further comprises an application head which is mountable on an eye and attached to the articulated arm; and the light projector is arranged in the application head.

14. The ophthalmological apparatus of claim 1, wherein the ophthalmological apparatus further comprises a base station and an application head which is mountable on an eye; the light source is arranged in the base station; one end of the articulated arm is attached to a housing of the base station; the application head is attached to another end of the articulated arm; and the light projector is arranged in the application head.

15. The ophthalmological apparatus of claim 14, wherein the scanner is arranged in the base station.

16. The ophthalmological apparatus of claim 1, wherein the light source comprises a femtosecond laser.

17. The ophthalmological apparatus of claim 1, wherein the articulated arm comprises a number of arm elements, in each case two of the arm elements being connected by way of an articulated module such that they can be rotated in parallel planes relative to one another.

18. The ophthalmological apparatus of claim 1, wherein the articulated arm comprises a number of arm elements, at least one of the arm elements being rotatable about its longitudinal axis.

19. The ophthalmological apparatus of claim 1, wherein the articulated arm comprises a number of arm elements, in each case two of the arm elements being connected by way of an articulated module, deflecting mirrors being fitted in the articulated modules and configured to transmit the deflected light pulses from one arm element to another arm element.

20. The ophthalmological apparatus of claim 1, wherein the ophthalmological apparatus is integrated in an eximer laser system.

21. The ophthalmological apparatus of claim 4, wherein the regulation module is configured to control rotation of the scanning plane to compensate rotations of the scanning direction which are caused by movements of the articulated arm.

* * * * *